United States Patent [19]

Schwarz

[11] 4,040,536

[45] Aug. 9, 1977

[54] LOCKING HARD GELATIN CAPSULE

[75] Inventor: Erwin Schwarz, Eberbach, Baden, Germany

[73] Assignee: R. P. Scherer Corporation, Detroit, Mich.

[21] Appl. No.: 574,324

[22] Filed: May 5, 1975

[51] Int. Cl.[2] ........................ A61B 19/02; B65D 43/10

[52] U.S. Cl. .......................................... 220/8; 206/530

[58] Field of Search ............................ 220/8; 206/530

[56] References Cited

U.S. PATENT DOCUMENTS

| | | | |
|---|---|---|---|
| 525,845 | 9/1894 | Hobbs | 206/530 |
| 3,173,840 | 3/1965 | Hostetler | 206/530 |
| 3,399,803 | 9/1968 | Oglevee | 206/530 |
| 3,508,678 | 4/1970 | Graham | 220/306 |
| 3,664,495 | 5/1972 | Graham | 220/8 |

*Primary Examiner*—George E. Lowrance
*Attorney, Agent, or Firm*—Allegretti, Newitt, Witcoff & McAndrews

[57] ABSTRACT

A hard gelatin capsule, especially for medicaments, having a cylindrical body and a cylindrical cap that telescopes over the open end of the body in which the interior surface of the cap, which overlaps the body, is provided with toothlike projections spaced around the circumference thereof to lock the body and cap against relative axial and rotational movement. In a preferred form of the invention the projections have gently-sloping side walls in both the lateral (circumferential) and longitudinal (axial) directions, which facilitate removing the cap from the dipping pin on which it is formed.

4 Claims, 6 Drawing Figures

LOCKING HARD GELATIN CAPSULE

PRIOR ART

Capsules consisting of telescopic parts have been known for a long time. U.S. Pat. No. 525,845 of 1894 describes a telescopic capsule, comprising a cap, having an annular constriction approximately in the middle and flares toward its open end. The capsule body is designed to be embraced by the annular constriction when the parts of the capsule are fitted together. This allegedly results in a good fit of the cap of the capsule on the body thereof.

In another capsule, such as is shown in U.S. Pat. No. 2,718,980, the capsule cap has on its inside an annular projection and an annular groove. The capsule body is also provided adjacent to its opening with an annular projection and an annular groove. A reliable seal between the cap and body of the capsule is allegedly ensured in that the projection and groove of one part of the capsule snap into the groove and projection of the other capsule part when these parts are pushed one into the other.

Both the capsule cap and the capsule body of the capsule described in the German Patent Specification 1,536,219 are formed with an annular constriction. When the two parts of the capsule are fitted one into the other, the convex annular bead formed on the inside of the capsule cap in conjunction with the constriction enters the annular constriction of the capsule body.

Capsules for containing medicaments are generally made today from hard gelatin in a dipping process. In this process, properly designed pins are dipped into an aqueous solution of gelatin and are subsequently withdrawn from the gelatin solution. When the gelatin has dried on the pin, the gelatin body is stripped from the pin and the resulting capsule part is cut to the desired length. In this practice it has been found that annular convex projections or concave recesses on the pin render the stripping of the gelatin body more difficult. Besides, it is almost impossible to obtain an airtight seal between the capsule cap and the rim of the capsule body when capsule parts are fitted together. This is due to the length tolerances of the capsule parts, particularly to the different distances between the rim and the annular recess of the capsule body. For a reliably fitting joint, the mating annular concave recesses or convex projections must interengage although this does not ensure an airtight seal.

SUMMARY OF THE INVENTION

It is an object of the invention to provide a telescopic capsule which can be manufactured from gelatin in such a manner that the above-mentioned difficulties are avoided. Besides, the capsule parts, regardless of length tolerances due to their manufacture, should be adapted to be fitted one into the other in conjunction with the filling operation so that a reliable seal is obtained, which is not broken when the capsules are packaged, transported and subsequently treated, e.g., on sealing machines, and which is airtight. This is accomplished by providing toothlike projections on the inside overlapping surface of either the body or cap which projections bear against the opposed surface of the body or cap, as the case may be.

When the toothlike projections engage the opposite wall of the capsule, the elasticity of the gelatin is utilized and the opposite part of the capsule is slightly deformed. The compression of the toothlike projections prevents a pulling apart of the parts of the capsule in the longitudinal direction as well as rotation of said parts relative to each other. The toothlike projections need be provided only over part of the periphery of the capsule.

The construction of the invention facilitates, above all, the stripping of the capsule parts from the dipping pin compared to capsule parts which have a continuous annular recess because the strippers can better slide over the toothlike recesses in the dipping pins than over concave recesses.

Another problem has also been solved by the invention. The parts of previously known capsules tend to separate when the capsules are assembled after having been filled because the assembling of the parts results in compression of air, which tends to force the parts of the capsules apart. For instance, German Patent Application P 22 32 236 describes an attempt to prevent compressing air within the capsule. This obviously adversely affects the tightness of such capsules. In the capsules, according to the invention, no air can be compressed which would promote a separation of the parts of the capsule because when the parts of the capsule are fitted together the air can escape between the toothlike projections until the very end of the assembling operation, when airtightness is achieved.

In a preferred embodiment, the toothlike projections are provided only on the inside surface of the cap of the capsule. In this case only the dipping pins used to make the capsule caps must be provided with corresponding toothlike recesses and the cap parts can easily be stripped from the dipping pins. If the capsule bodies were also provided on the outside with corresponding, outwardly directed, toothlike projections, the dipping pins for the capsule bodies would have to be provided with corresponding, outwardly directed toothlike projections. Whereas this design is also within the scope of the invention, it is more diffcult in this case to make the dipping pins and to strip the capsule bodies provided with such teeth from the dipping pins.

As stated above, many of the previously known capsule caps were provided with an inwardly facing, annular convex projection for interengaging with the capsule body. Manufacturers possess large quantities of properly shaped dipping pins for use in the manufacture of such capsule caps having concave recesses. These dipping pins can be used to make the capsules according to the present invention if toothlike recesses are formed in the concave recesses of the dipping pins for the cap parts. According to a further feature of the invention, the toothlike projections of the capsule caps are provided on the inside of a continuous peripheral convex projection.

DETAILED DESCRIPTION

An embodiment of the invention will now be described more fully with reference to the drawings.

Figure 1:
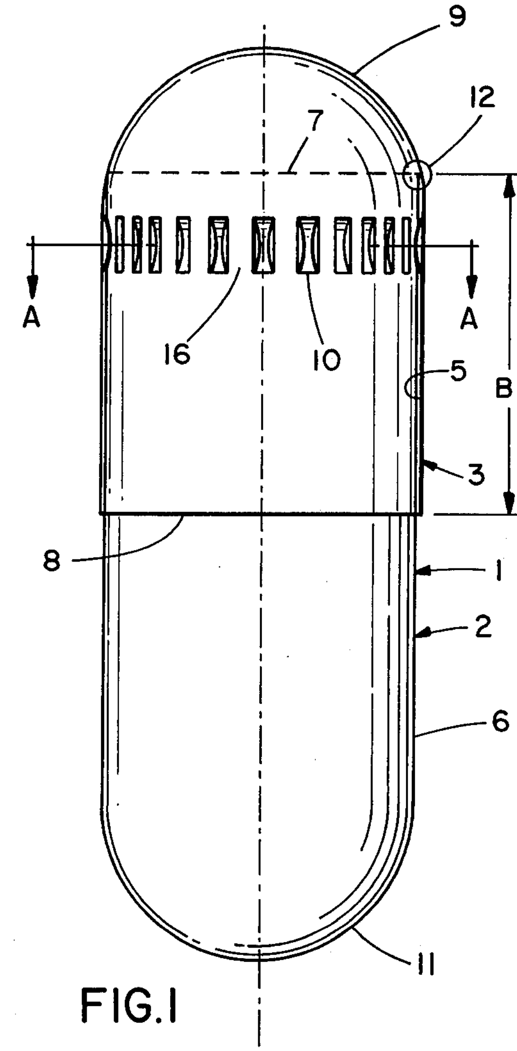
FIG. 1 shows a capsule fitted together.
Figure 4:
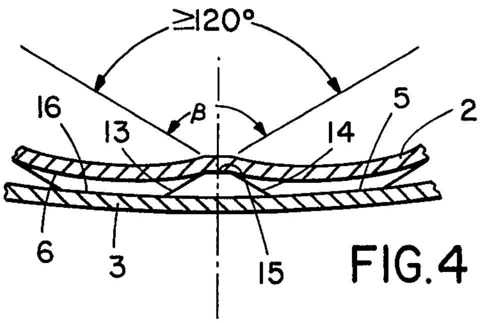
FIGS. 4 and 5 are transverse sectional views taken on lines B—B and C—C in FIG. 3.

FIG. 1 shows a capsule 1, which comprises a capsule body 2 and a capsule cap 3. At their open ends, the capsule cap 3 and the capsule body 2 terminate in rims 8 and 7, respectively. The closed ends of the two parts are designated 9 and 11, respectively, and are spherically shaped. Other end shapes may also be used. The capsule cap has an inside surface 5 and the capsule body has an outside surface 6.

Adjacent to the body portion B1 which is overlapped by the capsule cap 3, the latter has an angular portion B2, which is formed with inwardly directed, toothlike projections 10, the longitudinal axes of which are substantially parallel to the center line of the capsule cap 3.

When the capsule body 2 is fitted into the capsule cap 3, the rim 7 of the plain capsule body 2 slides past the portion B2. The capsule body 2 can be pushed into the capsule cap 3 until the rim 7 engages the inside surface of the closed end 9 of the capsule cap 3.

It is apparent that this results in an airtight peripheral seal at 12 between the rim 7 of the capsule body 2 and the inside surface 5 of the capsule cap 3. Because the capsule according to the invention has no annular concave recesss or convex projections which must interengage to seal the capsule, the length tolerances which are inevitable in the manufacture of any such capsule will not be significant. The airtight seal 12 between the capsule body 2 and the capsule cap 3 is relatively independent of the distance between the annular portion B2 of the capsule cap 3 and the rim 7 of the capsule body.

Figure 2:
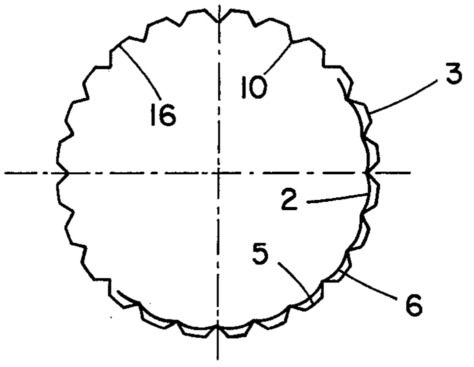
FIG. 2 is a transverse sectional view taken on line A—A in FIG. 1.

A reliable joint between the capsule cap 3 and the capsule body 2 is provided in that the toothlike projections 10 on the inside surface of the capsule cap 3 engage the outside surface 6 of the capsule body in the portion B1. It has been found that the engaging forces are sufficiently strong to prevent an opening of the capsule 1 when the same is packaged and when the packaged capsules are handled. FIG. 2 shows the toothlike projections 10 on the inside surface 5 of the capsule cap 3. These projections are distributed around the periphery of the inside surface 5 of the capsule cap 3 and engage the outside surface 6 of the capsule body 2 so that the surface 6 is slightly deformed, as is shown in FIG. 2 and so that the projections 10 define a continuous line of indentations about the circumference of body 2 having the appearance of a circumferential bead-like rib.

Figure 3:
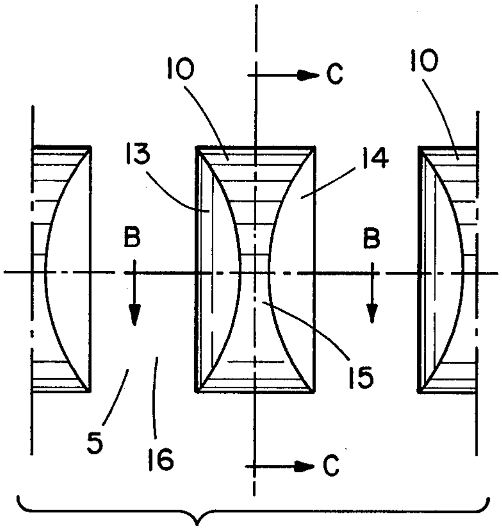
FIG. 3 is an enlarged view showing the toothlike projections as seen from the inside of the capsule cap.

From FIG. 3, two oblique side walls 13, 14 are apparent, which are connected by an intermediate portion 15. Alternatively, the side faces 13 and 14 could directly intersect so that there is no portion 15. The angle $\beta$ between the lateral side walls 13 and 14 should be at least about 120° and preferably at least 150°.

Figure 5:
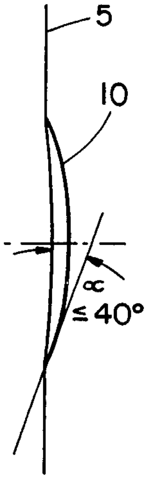

Particularly desirable results will be obtained if the angle of elevation $\alpha$, as is shown in FIG. 5, is not in excess of about 40°, preferably not in excess of 20°.

The selected angles are so large ($\beta$) or so small ($\alpha$) because the slope of the teeth should be as gentle as possible so that the capsule caps can easily be stripped from the dipping pins. Besides, the use of such gently-sloped teeth eliminates the formation of air bubbles between the dipping pin and the capsule cap during the dipping operation. The air disposed between the gently-sloped teeth can easily escape during the dipping operation.

For the same reason, spaces 16 are preferably provided between peripherally adjacent toothlike projections 10 so that there will be no sharp points between adjacent teeth. Sharp points render stripping of the capsule parts from the dipping pins and the escape of air more difficult. Besides, when the capsule parts are fitted together the wall material of said parts can easily deform and arch adjacent to the spaces 16 so that these portions contribute to a firm engagement of the toothlike projections and the latter ensure a reliable retention in spite of their flat shape.

The toothlike projections 10 are preferably provided in a number that can be divided by eight and at least by four. The fewer teeth are used, the larger may be the width of said teeth in the peripheral direction. Fewer teeth will also reduce the formation of air bubbles and will facilitate the penetration of the liquid gelatin between the teeth of the dipping pins. The use of teeth in a number which can be divided by four or eight teeth is desirable because the teeth can be formed on the dipping pins fixed on pin bars in this case by special tools which can laterally engage the dipping pins from opposite sides in two successive steps the positions of which are offset 90°.

Instead of providing the toothlike projections 10 throughout the periphery of the inside surface 5 of the capsule cap 3, only part of the periphery could be provided with toothlike projections 10.

It is apparent from the above that the invention permits the manufacture of a telescopic capsule which has a reliable joint. It is also apparent that an airtight seal between the capsule body and the capsule cap can be provided even if the dimensional stability of the individual capsule parts does not meet particularly close tolerances. This is an extraordinary advantage of this capsule because its manufacture is much simplified and many less rejects must be discarded than in the previous practice. The joint between the capsule body and the capsule cap is due to the engagement of the toothlike projections rather than to an interengagement of annular concave recesses and convex projections. For this reason the capsule body can always be pushed into the capsule cap to such an extent that an airtight seal is established between the rim of the capsule body and the inside surface of the cap. The toothlike projections hold the interfitting capsule parts against being pulled apart in the longitudinal direction and against relative rotation.

Within the scope of the invention the expression "toothlike projections" not only includes projections which are more or less pointed or cornered like teeth but includes also projections which are rounded projections of any shape whatever.

Figure 6:
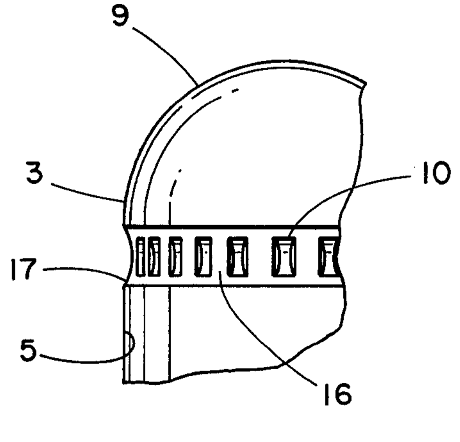
FIG. 6 shows a modification of the capsule cap, partly broken away.

FIG. 6 shows a continuous peripheral inwardly facing convex projection 17. The toothlike projections 10 are provided on the inside of this convex projection 17.

I claim:

1. A gelatin capsule for receiving a filling comprising, in combination:

a. a body having a closed end, a substantially cylindrical wall and an open end defining a sealing rim, and b. a telescoping cap having a closed end with an interior surface, a substantially cylindrical wall and an open end, the open end of the cap receiving the open end of the body with cap wall telescopically overlapping the body wall, said cap wall including a plurality of tooth-like spaced projections in a continuous row about the entire circumference of the cap wall, each of said tooth-like projections projecting inwardly to collectively define a circumferential bead-like rib, each of said tooth-like projections compressing the opposed portion of the body wall inwardly and simultaneously deforming the body wall outwardly intermediate the compressed portions to lock the cap against axial and rotational movement relative to the body upon positioning the rim against the interior surface of the cap to provide a substantially air tight seal, air spaces being provided between the tooth-like projections for escape of air upon assembly of the cap over the body.

2. The capsule of claim 1 wherein eight of said projections are provided on said wall.

3. The capsule of claim 1 wherein said tooth-like projections have sloping side walls in both lateral and longitudinal directions, the angle between opposed laterally sloping side walls being at least 120° and the angle of elevation of the longitudinal side walls is not in excess of 40°.

4. The capsule of claim 1 wherein said cap has an inwardly facing annular convex ridge on which said tooth-like projections are located.

* * * * *